_United States Patent_ [19]

Body et al.

[11] Patent Number: 5,193,533
[45] Date of Patent: Mar. 16, 1993

[54] HIGH-PRESSURE JET VENTILATION CATHETER
[75] Inventors: Simon C. Body, Roxbury; Stanley LeeSon, Newton, both of Mass.
[73] Assignee: Brigham and Women's Hospital, Boston, Mass.
[21] Appl. No.: 549,308
[22] Filed: Jul. 9, 1990
[51] Int. Cl.$^5$ .................. A61M 16/00; A61M 29/00
[52] U.S. Cl. ............................. 128/207.14; 604/105; 604/170; 604/281
[58] Field of Search .............. 128/204.24, 204.25, 128/207.14–207.17; 604/104–109, 95, 280–282, 164–170

[56] References Cited

U.S. PATENT DOCUMENTS

| | | | |
|---|---|---|---|
| 3,169,529 | 5/1963 | Koenig | 128/207.14 |
| 3,461,877 | 8/1969 | Morch | 128/207.14 |
| 3,734,083 | 5/1973 | Kolin | |
| 3,788,326 | 1/1974 | Jacobs | 128/207.15 |
| 3,896,804 | 7/1975 | Ekbladh et al. | |
| 4,315,513 | 2/1982 | Nawash et al. | |
| 4,593,687 | 6/1986 | Gray et al. | |
| 4,692,139 | 9/1987 | Stiles | |
| 4,807,626 | 2/1989 | McGirr | |
| 4,808,163 | 2/1989 | Laub | |
| 4,869,263 | 9/1989 | Segal et al. | 128/692 |
| 4,869,718 | 9/1989 | Brader | 604/164 |
| 4,895,561 | 1/1990 | Mahurkar | |
| 5,046,503 | 9/1991 | Schneiderman | 128/692 |

FOREIGN PATENT DOCUMENTS

| | | | |
|---|---|---|---|
| 1287885A | 2/1987 | U.S.S.R. | |
| 1424856 | 9/1988 | U.S.S.R. | 604/164 |

OTHER PUBLICATIONS

Stamey, T. A., "Suprapubic Cystostomy"; _Monographs in Urology_, 1 (1980), Stamey Percutaneous Suprapublic Catheter Sets.
Benjamin, B. and Gronow, D., "A New tube for Microlaryngeal Surgery"; _Anaesthesia and Intensive Care_, vol. VII, No. 3, Aug. 1979.
McKinney, et al., "A new technique for sleeve resection and major bronchial resection using twin catheters and high frequency jet ventilation"; 1988 Association of Anaesthetists of Gr. Britain and Ireland.
El-Baz, et al., "High Frequency Ventilation Through A Small Catheter for Laser Surgery of Laryngotracheal and Bronchial Disorders"; _Ann Otol Rhinol Laryngol_, 94:1985.
McClish, et al., "High-flow catheter ventilation during major tracheobronchial reconstruction"; _J. Thorac Cardiovasc Surg_, 89:508-512, 1985.
Scamman, et al., "Low Frequency Jet Ventilation for Tracheal Resection"; _Laryngoscope_, 96: Jun. 1986.
Salzer, et al., "Catheter Jet Ventilation, a Favorable Technique during Resection of the Central Tracheobronchial System"; _Thorac. Cardiovasc Surgeon_ 33, 1985.
Watanabe, et al., "The Clinical Value of High-Frequency Jet Ventilation in Major Airway Reconstructive Surgery"; _Scand J Thor Cardiovasc Surg_, 22:227–233, 1988.
Boyce, et al., "Vessel dilator cricothyrotomy for transtracheal jet ventilation", _Can J. Anasth_, 1989, 36:3/pp.350-3.

_Primary Examiner_—John D. Yasko
_Assistant Examiner_—Mark Bockelman
_Attorney, Agent, or Firm_—Sterne, Kessler, Goldstein & Fox

[57] ABSTRACT

A hollow flexible catheter designed for high pressure jet ventilation of the upper or lower larynx or trachea. The flexible catheter has a distal end and a proximal end, and houses a hollow flexible stylette which is slidably disposed in the catheter. There are a plurality of retractable flexible flanges integrally formed at the distal end of the catheter which bias outwardly to form a bulged or Malecot-type tip having gaps or spaces between the flanges when they are in their natural position. The stylette, which is slidably disposed in the catheter, can be extended towards the distal end of the catheter and used to retract the outwardly biased flanges, thereby reducing the outer diameter of the distal end of the catheter to aid in retraction or insertion of the catheter into the ventilating environment. The proximate end of the end of the catheter has means for connecting to a high pressure ventilation gas source, and the catheter can be used with a guide wire to further aid in the positioning of the catheter.

10 Claims, 4 Drawing Sheets

HIGH-PRESSURE JET VENTILATION CATHETER

FIELD OF THE INVENTION

The invention relates generally to a catheter designed for high-pressure jet ventilation. More specifically, the invention relates to a jet ventilation catheter for use during such procedures as laser surgery of the upper or lower larynx or trachea, tracheal resection surgery, lung transplantation, surgery during bronchial or pulmonary resection, microlaryngoscopy, or general and emergency trans-tracheal ventilation.

BACKGROUND OF THE INVENTION

During tracheal surgery it is important to maintain both adequate ventilation and oxygenation. However, standard technology for gas ventilation during open tracheal surgery poses several problems. First, proper ventilation and oxygenation requires large volumes of gas to be introduced. To facilitate introduction of sufficient volumes of gas, large diameter endotracheal or endobronchial tubes are often used. These large diameter tubes interfere with the surgeon's access to the trachea. Additionally, these large diameter tubes can be hazardous to the patient because of the risk of damage or trauma to the bronchial or tracheal wall due to potential impact with the tube.

High pressure jet air can be used with smaller diameter tubes to introduce an amount of air into the trachea equivalent to that produced by a much larger diameter tube. Various devices have been used during anesthesia to provide proper ventilation and oxygenation while simultaneously attempting to provide optimal unobstructed surgical access. The force exerted by a focused stream of exiting high-pressure jet gas against the wall of the carina or trachea may, however, cause possible harm to the patient. In addition, because of the instability of a small diameter catheter in the tracheal lumen there is potential for the distal end of the catheter to move or whip about as the high pressure gas is discharged from the tip of the catheter.

Previous efforts of using high-frequency or high-pressure ventilation through relatively small diameter catheters have resulted in devices which cause a focused high-pressure stream of gas exiting at the distal tip. Completely open orifices at the distal end of ventilation catheters are unacceptable due to this strong unidirectional gas flow at the catheter tip and the potential injury to the patient.

A device called the BEN-JET catheter, described by Dr. Bruce Benjamin et al., *Anaesth. Intens. Care*, 7:258-263 (1979), was developed to solve the potential injury problems associated with jet ventilation catheters. The BEN-JET is now manufactured by Tuta Laboratories Pty. Ltd. of Sydney, Australia. The BEN-JET catheter employs the use of four soft plastic "petals" at the distal end. The purpose of these petals is to help maintain the distal end of the ventilation catheter in a central portion of the trachea and thereby prevent trauma to the tracheal wall and ensure even distribution of ventilation gas. In the BEN-JET catheter, the petals fold back toward the proximal end of the catheter and expose an unobstructed orifice at the distal end of the catheter tube. The high pressure gas exits this orifice directly into the trachea. Because the path of the gas stream is unobstructed, the tracheal wall is exposed to the full force of the high pressure stream. The BEN-JET device, therefore, has the disadvantage of exposing the tracheal wall to the full force of the jet ventilation gas as it exits the catheter in a unified stream. This disadvantage is common in the prior art. It is a general object of this invention to provide an apparatus having a structure which overcomes this disadvantage by protecting the wall of the trachea from the potential injury created by the strong force of exiting high-pressure jet gas or by the possible whipping or lashing also caused by the exiting gas.

The unique construction of the invention provides for several prominent advantages over the prior art. First, the catheter outflow orifice is housed in a plurality of outwardly biased flanges terminating in a distal tip which divert the unidirectional flow of the high-pressure oxygen jet stream and cause the gas stream to disperse through gaps between the flanges, thereby reducing the force of the gas against the tracheal wall. Second, the catheter has retractable flanges which minimize damage to the trachea or bronchi during insertion or withdrawal of the catheter. Third, the catheter has a flexible internal stylette allowing the catheter to be bent into different shapes for ease of insertion and withdrawal. Fourth, the flexible stylette is hollow and allows for insertion or change of the catheter over a flexible, metal guide wire. In addition, the catheter may be of a longer length than prior art catheters allowing passage into the distal airways from an oral intubation.

SUMMARY OF THE INVENTION

Generally, the present invention relates to a high pressure ventilation catheter. The catheter is hollow and flexible, having a distal end and a proximal end. A stylette which is flexible and hollow is slidably disposed along the longitudinal axis of the catheter. At the distal end of the catheter, there are multiple flexible flanges which are integrally formed and biased outwardly to form a bulged circular or other oval shape, such as a Malecot-type tip. In one embodiment of the invention, there are four retractable flanges forming the distal tip.

At the extreme distal end of the catheter, there is a distal tip formed where the flanges terminate. The distal tip has a small orifice of dimensions sufficient to allow a guide wire to pass through it while simultaneously creating a barrier to the stylette when it is extended outwardly towards the distal end of the catheter. The catheter also has a means for introducing gas into the proximal end of the catheter. In one embodiment of the invention, such means would be a Luer lock connector.

The flanges are made of a flexible resilient material and are biased outwardly in their natural state. In one embodiment of the invention, the outwardly biased flanged distal end is constructed such that the flanges are in a semi-circular configuration. In an alternate embodiment, the flanges may be of a hinged or geometric configuration, while still being biased outwardly. The flanges are constructed such that they "memorize" their natural outwardly biased state. Therefore, upon being deformed by external forces, the flanges return to their natural outwardly biased state. In all the embodiments of the invention, the flanged, or bulged, distal end reduces potential injury to the trachea by providing flexible cushioning via retractable flanges. In their natural, outwardly biased position, the flanges help center the ventilation catheter in the trachea. These flanges can then be retracted to facilitate ease of insertion and withdrawal of the ventilation catheter.

When the flanges are radiating outwardly in their normal position, gaps are formed between the flanges. These gaps serve as exhaust ports for the exiting high pressure jet gas. The gas flow to be introduced into the trachea enters the catheter at the proximal end, flows through the catheter tube and exits the distal end in two stages. First, the gas exits the hollow catheter tube at a point inside the bulged space created by the flanges. Second, the gas passes from the bulged space through the orifices created between the bulging flanges and into the environment surrounding the distal portion of the catheter.

The extreme distal end of the catheter has a small orifice sufficient enough to allow a guide wire to pass through it, but small enough to obstruct passage of the internal stylette.

DETAILED DESCRIPTION OF A PREFERRED EMBODIMENT OF THE INVENTION

Figure 1:
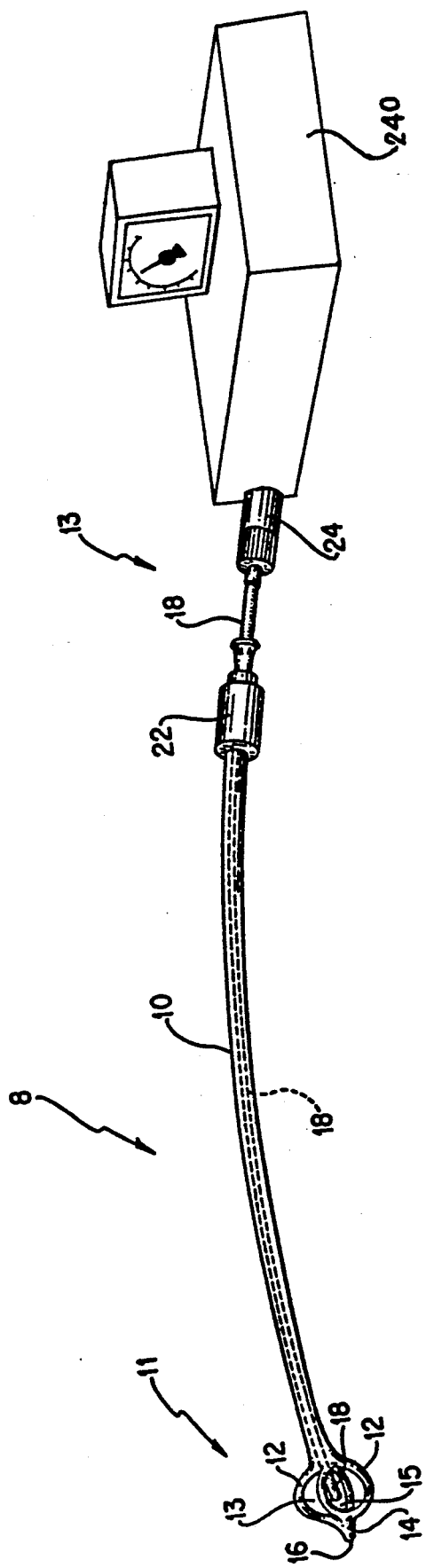
FIG. 1 is a perspective view of the jet ventilation catheter of the present invention.

Referring to FIG. 1, the jet ventilation catheter, designated generally as (8), comprises a hollow flexible catheter tube (10) with a hollow flexible stylette (18) disposed within the catheter tube (10). The catheter tube (10) has a distal end (11) and a proximal end (13). The catheter tube (10) should be constructed of flexible plastic or metal material capable of withstanding a pressure sufficiently high to perform ventilation. The material should be biologically inert and conform with the American National Standard for Anesthetic Equipment-Tracheal Tubes, ANSI 279.14-1983. In the preferred embodiment, the internal diameter of the catheter tube (10) should be of a sufficient size to provide at least a 30 liter per minute gas flow when attached to a 60 psi gas source at the proximal end (13). The internal radius of the stylette (18) should be large enough to allow a wire guide (20) to pass through it for aid in the exchange or insertion of the catheter (8) into the trachea (30).

The distal end (11) of the catheter tube (10) has a plurality of retractable flanges (12) which are integral with, and terminate at, the distal tip (14) of the distal end. The distal end (11) of the catheter (8) is constructed so that the flanges (12) are naturally biased outwardly forming a flanged "Malecot-type" tip, similar to that generally disclosed in Stamey, T. A., "Suprapubic Cystostomy" in *Monographs in Urology*, 1 (1980). Therefore, the normal position of the flanges (12), as shown in FIG. 1, is in a radially dispersed configuration whereby there are open spaces or gaps (13) separating the individual flanges (12). A hollow flexible stylette (18) is disposed throughout the catheter tube (10) along its longitudinal axis and is slidably positioned therein. Located at the proximal end of the catheter (13) are means for introducing gas into the proximal end of the catheter, such as that providing connection with a high-pressure jet ventilation gas source (240). In the preferred embodiment, these means for connection to a high-pressure jet ventilation gas source is comprised of a standard Luer lock connector (24) to suitable dimensions. Such a Luer lock connector and a gas source are depicted in FIG. 1. Naturally, connectors and gas sources other than those specifically shown in the drawing may also be use to practice the invention.

At the extreme distal end of the catheter is a distal tip (14) having a relatively small opening or orifice (16). The orifice (16) in the distal tip (14) is large enough to allow a wire guide (20) to extend through it to aid in the positioning of the catheter; however, the orifice (16) is of a diameter smaller than that of the flexible stylette (18). This construction causes the distal tip (14) to act as a barrier restricting the axial movement of the flexible stylette (18) through the catheter tube (10) beyond its distal end (11). This unique tip structure provides means for retraction of the flexible flanges (12) by sliding the flexible stylette (18) towards and into the distal tip (14) of the catheter tube (10) which pushes the distal tip (14) outward, elongating the distal end (11). As the distal tip (14) is pushed outwardly along the axis of the catheter (8), the flanges (12), being fixed in length, are pulled inward, decreasing the overall diameter at the distal end of the catheter.

Figure 2:
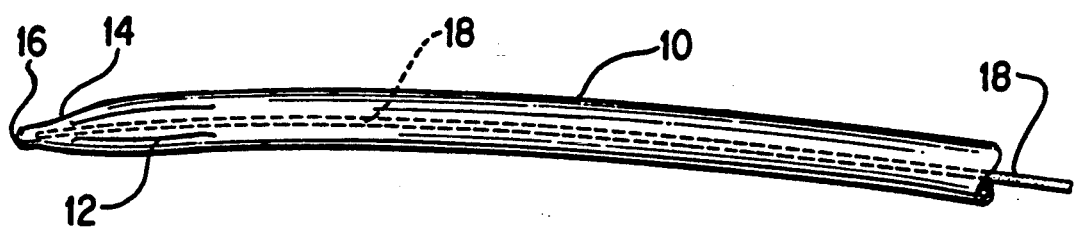
FIG. 2 is a perspective breakaway view of the distal end of the jet ventilation catheter having the distal tip extended by a stylette.
Figure 3:
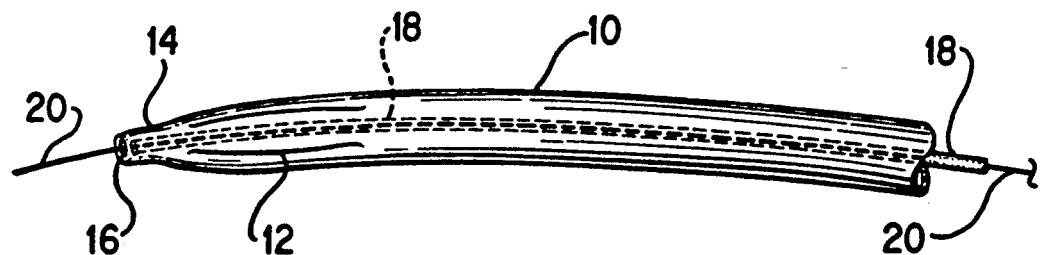
FIG. 3 is a perspective breakaway view of the distal end of the jet ventilation catheter having the distal tip extended by a stylette with a wire guide disposed through the stylette and extended through the distal tip of the catheter.
Figure 4:
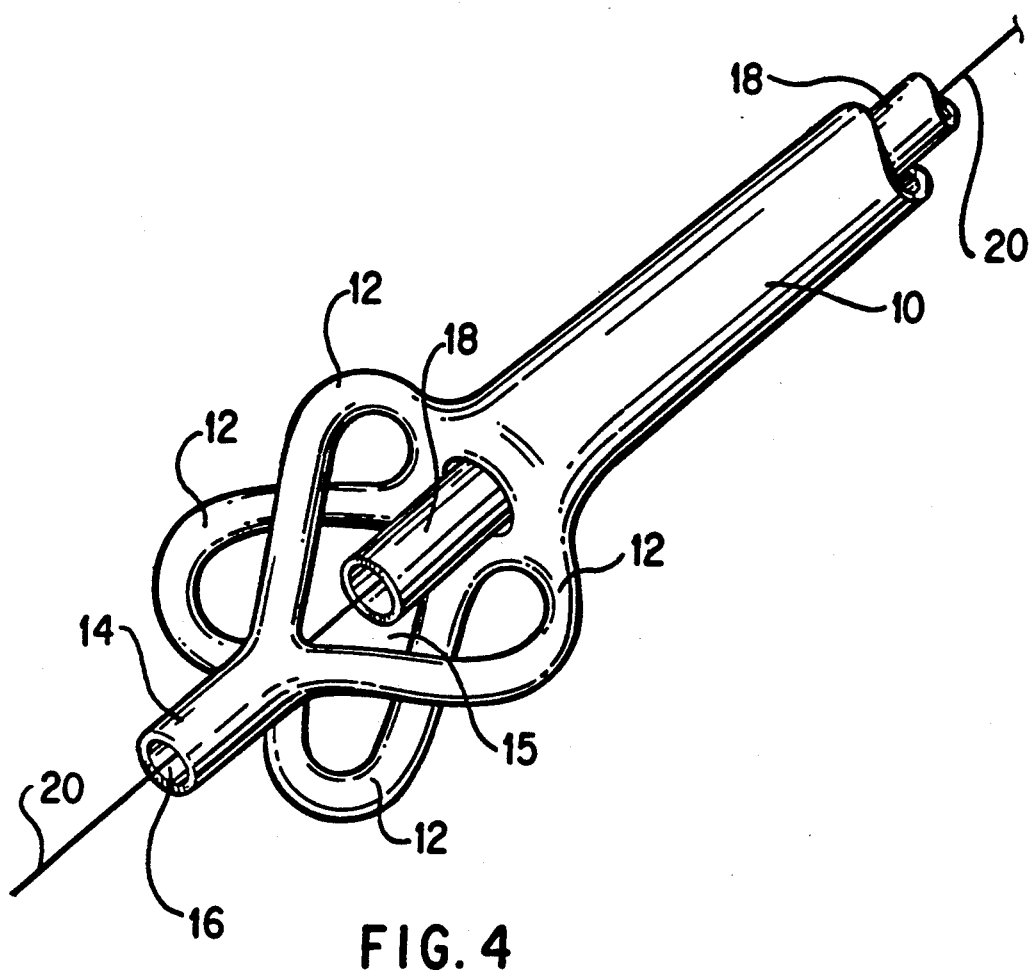
FIG. 4 is a perspective view of the distal end of the jet ventilation catheter with the flanges in their normal position, and having a wire guide extended through the distal tip.

FIG. 2 shows an embodiment of the invention with the flanges (12) fully retracted. FIG. 3 shows the invention with the flanges fully retracted and a guide wire (20) disposed through the stylette (18) and distal tip (16) of the catheter tube (10) for aid in insertion of the catheter. It should be noted that retraction of the flanges (12), by drawing in the flanges in towards the longitudinal axis of the catheter (8), reduces the size of the spaces or gaps (13) between the individual flanges (12). At the extreme extension of the distal tip (14), the flanges are drawn in to the point where the gaps (13) can be completely eliminated as shown in FIG. 2 and FIG. 3. The flanges (12) are made of a material which has a "memory" of their natural, outwardly biased position. Therefore, upon the removal of the pushing force on the distal tip (14) caused by axial movement of the stylette (18) the flanges return to their normal, outwardly bulged configuration.

As depicted in FIG. 3, when the flanges (12) are fully retracted, the reduced diameter of the distal tip (14) is such that the outer diameter at the flanged distal end of the catheter is approximately equivalent to the outer diameter of the catheter tube (10). This reduced diameter minimizes the risk of damage to the trachea or bronchi during insertion or withdrawal of the catheter. The force applied in extending the stylette (18), which in turn elongates the tip (14) and pulls in the flanges (12) along the axis of the catheter can be varied. Depending upon how far the stylette (18) is extended towards the distal end of the catheter (11), the outer diameter at the distal end can be varied depending upon the degree of deformation of the flanges from their natural position.

The catheter can be constructed in any length from 20 cm to 60 cm to be effective for its intended use. The catheter is constructed from a flexible plastic or metal material, preferably polyvinyl chloride (PVC) manufactured to conform with Z79 ANSI standards. In one embodiment of the invention, the catheter can be coated with a proper "laser proof" material such as that which is commercially available from Xomed Corp. of Jacksonville, Fla., under part number 70-57430, or it's equivalent, to provide a device suitable for use with laser surgery. In a preferred embodiment, the catheter is 40 cm in total length when the flanges are in their normal position. The preferred outer diameter of the catheter would be between 10 and 14 French gauge and constructed to have an opening (16) at the distal tip (14) to be a diameter sufficient to allow a 0.97 mm diameter wire guide (20) to pass through it. Preferably the distal tip has a length of between 1 and 10 mm. The opening (16) can be made to accommodate different sized wire guides if desired. Also in the preferred embodiment of the invention, the radially dispersed flanged distal end (11) would have an outer diameter of between 10 and 20 mm when the flanges (12) are in the normal position. Each flange would have a total length of between 1.3 cm and 2.5 cm. Preferably, the distal end would incorporate four flanges in a symmetrical manner forming a bulged tip configuration. Alternatively, any number of flanges can be used.

Figure 5:
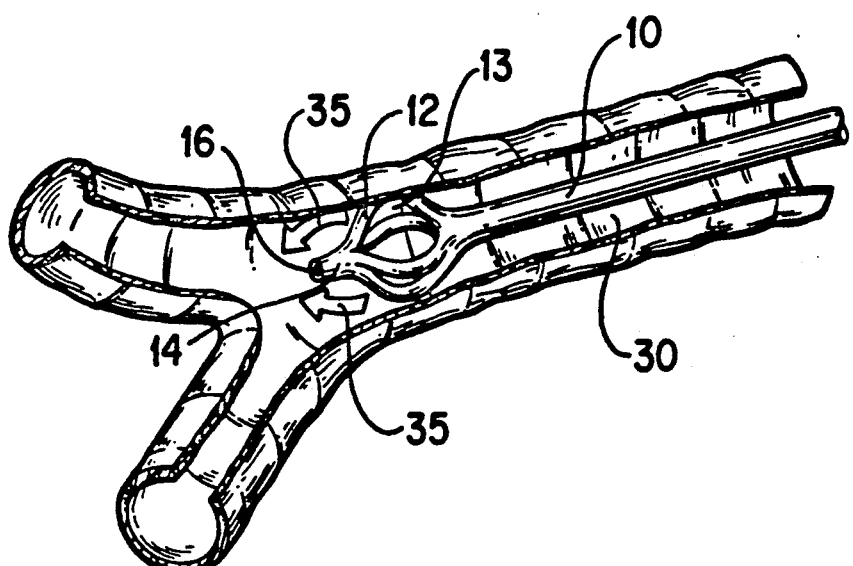
FIG. 5 is a perspective view of the jet ventilation catheter inserted in a trachea with the flanges in their normal position and protecting the walls of the trachea from direct exposure to the high-pressure ventilation gas stream, the gas stream shown by arrows.

As depicted in FIG. 5, in addition to the flanges (12) providing a cushion or bumper when in the normal position, the unique structure of the catheter protects the wall of the trachea (30) from direct impingement by the high-pressure jet air being introduced through it. FIG. 5 shows the catheter (8) inserted into the trachea (30). When the flanges (12) are in the normal position, the tubular portion of the catheter tube (10) terminates at its distal end inside the space (15) formed when the flanges are bowed outwardly. Normally, gas ventilation is conducted when the catheter is positioned in the trachea and the flanges (12) are in the normal position. Gas flowing from a high pressure source through the catheter (8) exits the tubular portion of the catheter tube (10) inside the space formed inside the flanges (15), and is then required to disperse radially as shown by arrows (35) to exit into the patient's airway via the openings (13) created between the bowed flanges (12). The extreme distal tip of the catheter (14), having a relatively small opening (16), prevents all but a very small portion of the gas flow from exiting in a direct line through the distal end of the catheter. This unique structure protects the tracheal wall from being exposed to the full force of the direct high-pressure air stream exiting from the tubular portion of the catheter tube (10). The arrows in FIG. 5 show the possible paths of the existing high-pressure jet gas.

In one mode of operation, once the patient is properly prepared, a flexible guide wire (20) is inserted into the trachea (30). The jet ventilation catheter (8) and internal stylette (18) are then passed over the guide wire (20) into a desired position in the trachea (30). As the catheter (8) is passed along the guide wire (20) and into the trachea (30), the flange(s) (12) are usually retracted to aid insertion of the catheter. To retract the flanges (12), the stylette (18) is extended by applying axial force to the proximal end of the stylette, causing the stylette to slide towards the distal end (11) of the catheter until the distal end of the stylette (18) comes into contact with the distal tip of the catheter (14). In one embodiment of the invention, positioning means (22) can be secured near the proximal end of the catheter tube (10) to help the user restrain axial movement of the catheter tube (10) while axially sliding the stylette (18).

Figure 6:
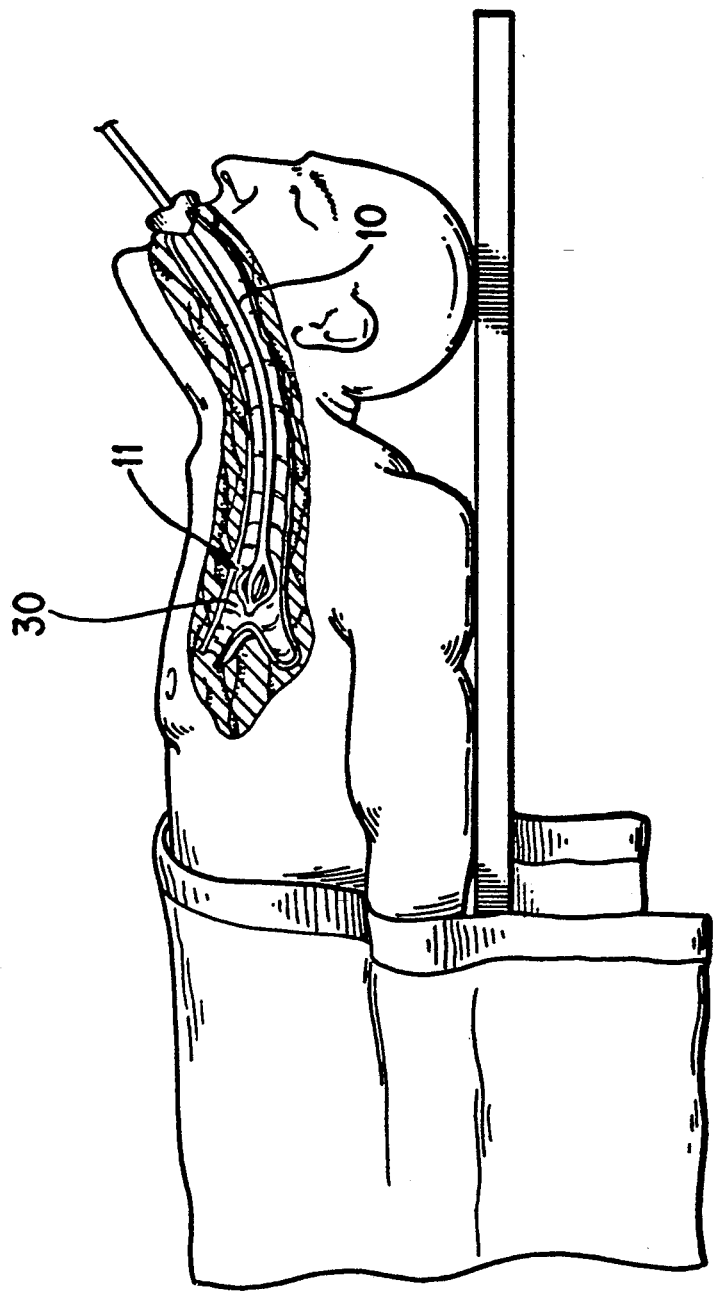
FIG. 6 is a side view of the distal end of the jet ventilation catheter positioned in a patient.

The distal tip (14) acts as a barrier to the distal advance of the stylette. As the stylette (18) is extended further towards the distal end of the catheter, the stylette pushes the tip (14) outward along the longitudinal axis of the catheter (8) thereby pulling in the flanges (12) along the longitudinal axis of the catheter. As the flanges (12) are pulled in, the outer diameter of the distal end of the catheter (11) is reduced. Once in the correct position, normally in the posterior commissure of the larynx as depicted in FIG. 6, the longitudinal force being exerted on the stylette (18) causing it to move towards the distal end (11) is removed and the flanges (12) are allowed to return to their normal outwardly biased position thereby securing and centering the catheter (8) in the trachea (30). The guide wire (20) can then be removed.

In another mode of operation, no wire guide (20) is used. The internal stylette (18) is inserted into the jet ventilation catheter (8) and the flanges (12) are retracted as described previously. The stylette (18) and catheter (8) as a whole are introduced into the trachea (30) via the larynx. The stylette (18) their normal position securing the catheter (8) in the trachea (30).

In both these modes of operation, once the catheter (8) is in the desired position, the proximal end of the catheter (13) can be attached to a high pressure gas source using a Luer lock connector (24) or suitable substitute. The patient can then be ventilated, as depicted in FIG. 6, without the possibility of the full force of the jet air stream being absorbed by any specific area of the tracheal wall. After the applicable surgical operation is performed and the patient is ready for extubation, the catheter (8) can be removed. Removal can be accomplished by reintroducing the stylette (18), retracting the flanges (12) by extending the stylette towards the distal end of the catheter (11), and extracting the catheter (8) out of the patient.

The foregoing description of the preferred embodiments of the invention have been presented for purposes of illustration and description. It is not intended to be exhaustive or to limit the invention to the precise form disclosed, and obviously many modifications and variations are possible in light of the above teaching. For example, the flanges (12) can be constructed having an outward bias structure other than a semicircular configuration including hinged, elliptical, or otherwise. Further, substitutes for a Luer lock connector could be used, or alternatively, the invention may lack a connector at the proximal end. The embodiments chosen and described in this description were selected to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A ventilation system comprising:
   (a) a hollow, flexible catheter having a distal end and a proximal end;
   (b) a hollow, flexible stylette slidably disposed in said catheter;
   (c) a plurality of retractable, flexible flanges integrally formed at the distal end of said catheter, said flanges being biased outwardly in their natural state and terminating at a distal tip formed at the extreme distal end of said catheter, said tip having an orifice large enough to allow a wire guide to pass through said tip but small enough to prevent said stylette from penetrating through the tip as the stylette is extended towards the distal end of the catheter along the axis of said catheter;

(d) a gas source capable of delivering gas of sufficiently high pressure for ventilation; and (e) means for connecting the proximal end of said catheter to said gas source.

2. A ventilation system as recited in claim 1, wherein said means for connecting the proximal end of said catheter to said gas source comprises a gas tight locking connection.

3. The ventilation system of claim 1 wherein said gas source is capable of delivering gas at a pressure of 60 psi.

4. The ventilation system of claim 1 further comprising means for retracting said flexible flanges.

5. A ventilation system as recited in claim 1 wherein said flanges are biased outwardly in a bulged oval shape.

6. A ventilation system as recited in claim 1 or 5, wherein said catheter has a length of between 20 to 60 cm.

7. A ventilation system as recited in claim 5, wherein said catheter is constructed having an outer diameter of French gauge size between 8 and 16.

8. A ventilation system as recited in claim 5, wherein said distal end of said catheter is comprised of four of said flexible flanges, each of said flexible flanges having a length of between 13 and 2.5 centimeters.

9. A ventilation system as recited in claim 8, wherein said tip is between 1 and 10 millimeters in length.

10. A ventilation system comprising:

(a) a gas source capable of delivering gas of sufficiently high pressure for ventilation;

(b) a hollow, flexible catheter having a distal end and a proximal end, said proximal end of said catheter removably connected to said gas source and said distal end of said catheter having a plurality of curved, retractable flanges biased outwardly forming a bulged tip configuration;

(c) a distal tip having a small orifice large enough to allow a wire guide to pass through it, said flanges being constructed of a soft resilient material and connecting said catheter tube to said distal tip; and (d) a hollow, flexible stylette slidably and removably disposed in said catheter tube, said stylette having an inner diameter great enough to allow a wire guide to pass through it, and an outer diameter larger than said orifice.

* * * * *